United States Patent [19]

Feld

[11] Patent Number: 4,539,852
[45] Date of Patent: Sep. 10, 1985

[54] VIAL CAP TORQUE TESTER

[75] Inventor: Jerome H. Feld, Brooklyn, N.Y.

[73] Assignee: E. R. Squibb & Sons, Inc., Princeton, N.J.

[21] Appl. No.: 589,800

[22] Filed: Mar. 15, 1984

[51] Int. Cl.³ .......................... G01N 3/22; G01L 5/00
[52] U.S. Cl. .................................. 73/847; 73/862.01; 73/862.19; 81/3.4
[58] Field of Search ........... 73/862.01, 862.08, 862.19, 73/862.23, 841, 842, 843, 845, 846, 847, 848, 856, 761; 81/3.38 R, 3.39, 3.34

[56] References Cited

U.S. PATENT DOCUMENTS

| | | | |
|---|---|---|---|
| 2,279,698 | 4/1942 | Weckerly | 73/847 |
| 2,300,288 | 10/1942 | Hullhorst | 73/862.08 X |
| 2,337,951 | 12/1943 | Whitehead | 73/761.1 X |
| 2,779,187 | 1/1957 | Stewart | 73/862.19 X |

Primary Examiner—Charles A. Ruehl
Attorney, Agent, or Firm—Lawrence S. Levinson; Sanford J. Asman

[57] ABSTRACT

A device for testing the torque required to break the seal of a medicine vial is comprised of a torque gauge mounted on a base. The torque gauge has an armature which is adapted to hold the bottom of a medicine vial. A torque arm is attached to a cylindrical unit made up of a housing and a concentric handle connected together by a coil spring such that the coil spring can be opened by turning the housing relative to the handle so that the spring fits over the cap of a vial and holds it securely when turned in a direction which tends to tighten the coils of the spring.

3 Claims, 4 Drawing Figures

VIAL CAP TORQUE TESTER

BACKGROUND OF THE INVENTION

The present invention relates to a torque tester for use in measuring the torque required to turn an aluminum cap on a vial. In particular, the present device is used to measure the torque used to move the cap on a medicine vial.

Medicine vials are typically glass vials which are stoppered with a rubber stopper which fits into the opening in the neck of the vial. The top of the rubber stopper typically has a flange which extends over the top surface of the neck of the vial. When vials are filled with medicine, a rubber stopper is inserted into the neck of the vial, whereby the compression of the neck of the stopper provides a seal on the vial. An aluminum cap is then applied over the top of the rubber stopper. A machine is used to crimp the skirt of the aluminum cap under the vial neck flange, whereby the rubber stopper flange is compressed. The compression of the rubber stopper flange provides additional sealing on the vial and assures retention of the stopper.

In order to perform quality control tests regarding the adequecy of the seal on closed vials, it has been proposed that a device capable of measuring the torque required to turn the aluminum cap on the sealed vial would provide a measure related to adequecy of the seal of the vial. Accordingly, a device capable of measuring the torque required to turn the cap on the vial is required.

SUMMARY OF THE INVENTION

The present invention is a vial cap torque tester which is capable of measuring the torque required to turn a cap, typically made of aluminum, on a rubber stoppered vial. The torque tester of the invention is comprised of a base which holds a torque gauge. The torque gauge has a gripper adapted to hold the bottom of a vial thereon. The device is further comprised of an apparatus for attaching to and turning the cap of the vial. That device is comprised of a spring having an inner diameter which is somewhat less than the outer diameter of the aluminum cap which compresses the rubber stopper on the vial. The spring is attached to a cylindrical handle at one end and to a concentric cylindrical housing at the other end. A torque arm is connected to the cylindrical housing such that by turning the torque arm relative to the cylindrical handle in a direction which opens the coils of the spring, the spring can be placed over the cap. Subsequent release of the handle relative to the torque arm causes the spring to close down upon the cap. If a turning force is applied to the torque arm in the direction which closes the coils of the spring, the cap will be held tightly while the vial turns the torque tester to achieve a maximum torque prior to slippage of the cap on the vial. At the point of slippage of the cap on the neck of the vial, the maximum torque registered by the torque gauge indicates the actual amount of torque required to cause slippage of the cap.

DETAILED DESCRIPTION OF THE PREFERRED EMBODIMENT

Figure 1:
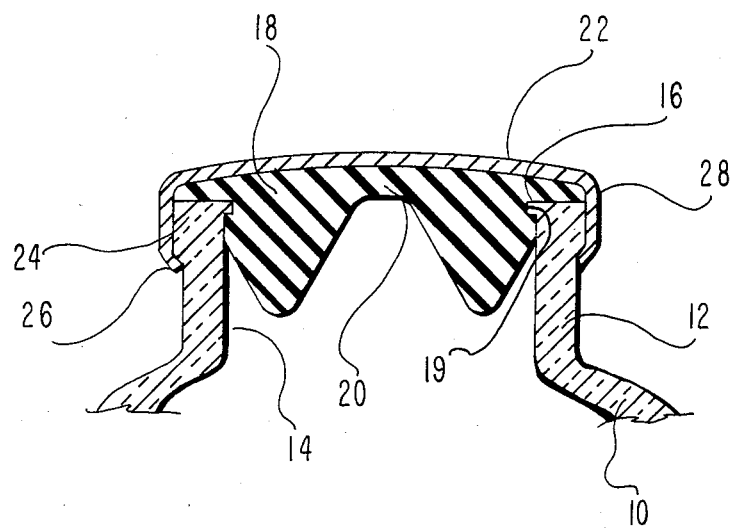
FIG. 1 is a cross-sectional view of the neck of a vial having a stopper and aluminum cap thereon of the type used with the present invention.

Referring generally to FIG. 1, a cross-sectional view of a portion of a medicinal vial 10 is shown. The vial 10 is typically manufactured out of glass in a manner well-known in the art. The vial 10 has a substantially cylindrical neck 12 having a substantially cylindrical inside bore 14. On the top of the neck 12 some vials 10 have an internal flange 16 which extends around the inside of the bore 14. A rubber stopper 18 is used to seal the mouth of the vial 10, in a manner well known in the art. If the vial 10 has an internal flange 16, then the stopper 18 may have a corresponding undercut 19. Such stoppers 18 typically have a relatively thin portion 20 centrally located in order that they can be readily pierced by a hypodermic syringe. When the vial 10 is sealed, an aluminum cap 22 is crimped over the edge of the top 24 of the neck 12 whereby the skirt 26 of the cap 22 is tucked under the flange 24 of the neck 12.

Once a vial 10 has been securely closed in the manner illustrated in FIG. 1, a measure of the tightness of the seal provided by the rubber stopper 18 is related to the amount of torque which can be applied to the band portion 28 of the aluminum cap 22 before the cap 22 rotates on the vial 10.

Figure 2:
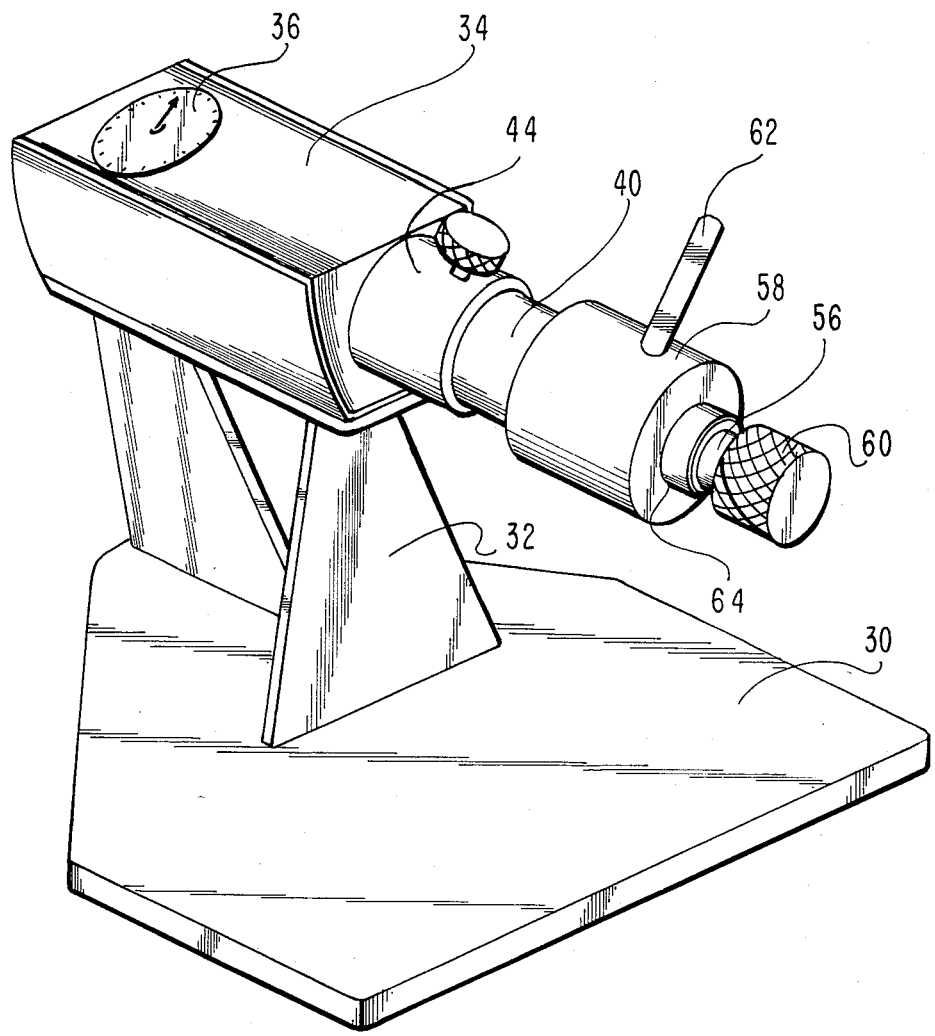
FIG. 2 is a perspective view of the present invention.

Referring now to FIG. 2, a pictorial view of the device of the present invention is shown. As illustrated, the device comprises a base 30 having a vertical support member 32 attached thereto. On the vertical support member 32, there is a dial torque gauge 34, such as Model TG manufactured by John Chatillon and Sons, 83-30 Kew Gardens Road, New York, N.Y. 11415. The dial torque gauge 34 has a dial 36 which reads the maximum torque indicated by the torque gauge 34 when the shaft (See FIG. 3) of the torque gauge 34 is rotated.

Figure 3:
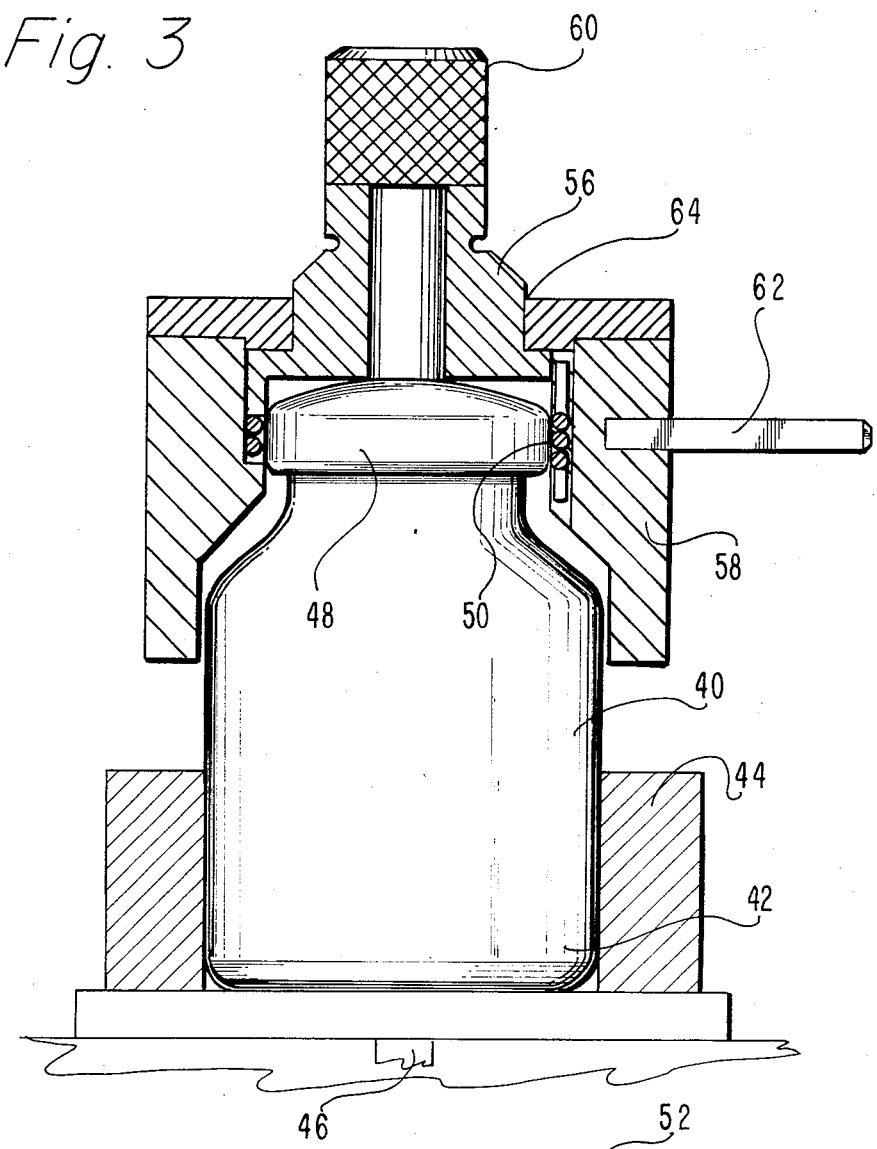
FIG. 3 is a partial cross-sectional view showing the present invention in operation.

Referring now to FIG. 3, a vial 40 is shown with its base 42 being securely held by a set of jaws 44 which are secured to the shaft 46 of the torque gauge 34. The aluminum cap 48, which is on the vial 40, is held by a spring 50 more fully illustrated in FIG. 4.

Figure 4:
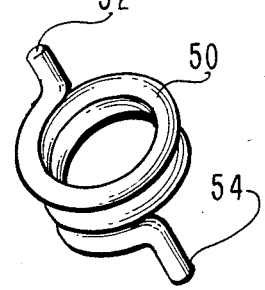
FIG. 4 is a perspective view of the spring used to grip the vial cap.

As shown in FIG. 4, the spring has a pair of tangs 52, 54 which are held by a cylindrical handle 56 and a cylindrical housing 58, respectively. The cylindrical handle 56 has a knurled portion 60, and the cylindrical housing 58 has a torque arm 62 attached thereto. The cylindrical handle 56 can be rotated within an opening 64 relative to the housing 58. Accordingly, when the knurled portion 60 of the handle 56 is rotated in the direction opposite that which the spring 50 is wound relative to the cylindrical housing 58, the inside diameter of the spring 50 expands somewhat. The spring 50 can then be fitted over the outside diameter of the aluminum cap 48. If the tension is then released on the handle 56 relative to the torque arm 62, any torque applied to the torque arm 62 in the direction in which the spring 50 is wound will be applied directly to the cap 48. Accordingly, the torque arm 62 can be turned in the direction in which the spring 50 is wound causing the shaft 46 of the dial torque gauge 34 to be turned. The reading on the dial torque gauge 34 increases until such time as the cap 48 slips relative to the vial 40. At that point the dial 36 on the torque gauge 34 will retain its maximum reading, which will be representative of the torque required to break the seal of the vial 40.

I claim:

1. A device for testing the torque required to turn the cap of a sealed vial comprising:
   (a) a base;
   (b) torque gauge mounted on said base, said torque gauge including means for securely holding the base of a vial;
   (c) means for releasably holding the cap of a vial, said means comprising a coil spring whose inside diameter is slightly smaller than the outside diameter of said cap when said spring is relaxed;
   (d) a substantially cylindrical handle attached to one end of said spring;
   (e) a substantially cylindrical housing attached to the other end of said spring, said cylindrical housing being concentric with said cylindrical handle whereby if said housing is turned relative to said handle in a direction opposite the direction in which said coil spring is wound, said coil spring may be opened sufficiently to extend over said cap of said vial so that said coil spring will securely hold said cap of said vial when said housing and handle are released; and
   (f) means for applying torque to said cap in in a direction which tends to close said coils of said coil spring such that said coil spring firmly holds said cap without slipping.

2. The device of claim 1 wherein said means for applying torque comprises a torque arm attached to said housing.

3. The device of claim 1 wherein said means for applying torque comprises a torque arm attached to said handle.

* * * * *